(12) United States Patent
Fukutani et al.

(10) Patent No.: US 8,687,868 B2
(45) Date of Patent: Apr. 1, 2014

(54) IMAGE GENERATING APPARATUS, IMAGE GENERATING METHOD, AND PROGRAM

(75) Inventors: Kazuhiko Fukutani, Yokohama (JP); Takuji Oishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 119 days.

(21) Appl. No.: 13/498,192

(22) PCT Filed: Dec. 8, 2010

(86) PCT No.: PCT/JP2010/007150
§ 371 (c)(1),
(2), (4) Date: Mar. 26, 2012

(87) PCT Pub. No.: WO2011/070778
PCT Pub. Date: Jun. 16, 2011

(65) Prior Publication Data
US 2012/0183190 A1 Jul. 19, 2012

(30) Foreign Application Priority Data

Dec. 11, 2009 (JP) ................................. 2009-281452

(51) Int. Cl.
*G06K 9/00* (2006.01)
*G03B 42/06* (2006.01)
*A61B 8/00* (2006.01)

(52) U.S. Cl.
USPC ................. 382/128; 73/597; 367/7; 600/437; 600/443

(58) Field of Classification Search
USPC .......................... 382/128–134; 73/597; 367/7; 600/437–461
See application file for complete search history.

(56) References Cited

U.S. PATENT DOCUMENTS

| 6,305,225 | B1 | 10/2001 | Bae et al. ........................ 73/602 |
| 7,864,307 | B2 | 1/2011 | Fukutani et al. ................. 356/73 |
| 8,144,327 | B2 | 3/2012 | Nakajima et al. ............. 356/432 |
| 2005/0004458 | A1 | 1/2005 | Kanayama et al. ........... 600/437 |
| 2005/0187471 | A1 | 8/2005 | Kanayama et al. ........... 600/437 |
| 2006/0235302 | A1* | 10/2006 | Grossman et al. ............ 600/443 |
| 2008/0173093 | A1 | 7/2008 | Wang et al. ..................... 73/602 |

(Continued)

FOREIGN PATENT DOCUMENTS

| CN | 1575770 | 2/2005 |
| CN | 1650794 | 8/2005 |

(Continued)

OTHER PUBLICATIONS

Office Action issued on May 31, 2013 in Chinese (PRC) counterpart patent application 201080055219.1, with translation.

(Continued)

*Primary Examiner* — Vu Le
*Assistant Examiner* — Soo Park
(74) *Attorney, Agent, or Firm* — Fitzpatrick, Cella, Harper & Scinto (57) ABSTRACT

An image generating apparatus of the present invention has a determination unit that sets a target area in a part of an area inside a subject, executes processing to adjust a phase of each detection signal based on a distance from each detection element to a target area and a tentative velocity, and calculate dispersion of intensities of a plurality of detection signals of which phases are adjusted, for a plurality of tentative velocities, and determines a velocity for which dispersion of intensities is minimum, out of the plurality of tentative velocities, as a propagation velocity.

11 Claims, 10 Drawing Sheets

(56) References Cited

U.S. PATENT DOCUMENTS

| | | | |
|---|---|---|---|
| 2008/0306371 A1 | 12/2008 | Fukutani et al. | 600/407 |
| 2009/0149761 A1 | 6/2009 | Zou et al. | 600/476 |
| 2009/0198128 A1 | 8/2009 | Fukutani et al. | 600/437 |
| 2010/0049049 A1 | 2/2010 | Asao et al. | 600/443 |
| 2010/0087733 A1 | 4/2010 | Nakajima et al. | 600/437 |
| 2010/0191109 A1 | 7/2010 | Fukutani et al. | 600/437 |
| 2010/0331662 A1 | 12/2010 | Fukutani et al. | 600/407 |
| 2011/0194380 A1 | 8/2011 | Fukutani | 367/140 |
| 2012/0130222 A1 | 5/2012 | Kobayashi et al. | 600/407 |

FOREIGN PATENT DOCUMENTS

| | | |
|---|---|---|
| CN | 101214156 | 7/2008 |
| CN | 101336832 | 1/2009 |
| CN | 101453939 | 6/2009 |
| EP | 1561424 A1 | 8/2005 |
| JP | S59-171542 | 9/1984 |
| JP | H08-317926 | 12/1996 |
| JP | 2000166925 A | 6/2000 |
| JP | 2007-301154 | 11/2007 |

OTHER PUBLICATIONS

M. Xu et al., "Photoacoustic Imaging in Biomedicine", Review of Scientific Instruments, AIP, vol. 77, No. 4, Apr. 17, 2006, pp. 041101-1-041101-22.

* cited by examiner

FIG. 6 ly progressing in medical fields. An example
IMAGE GENERATING APPARATUS, IMAGE GENERATING METHOD, AND PROGRAM

TECHNICAL FIELD

The present invention relates to an image generating apparatus, image generating method and program, for generating an image representing information inside a subject.

BACKGROUND ART

Research on imaging apparatuses which irradiate light from a light source (e.g. laser) onto a subject, such as living body, and visualize the information inside the subject, has been energetical of such a visualization technology using light is photoacoustic tomography (PAT). A photoacoustic tomography apparatus detects an acoustic wave (typically an ultrasonic wave) generated from a tissue of the living body, which absorbed energy of the light propagating in and diffusing from a subject, at a plurality of locations surrounding the subject. Then the obtained signals are mathematically analyzed, and the information related to the optical property inside the subject, particularly the absorption coefficient distribution, is visualized. Recently pre-clinical research on imaging the blood vessels of small animals using the photoacoustic tomography apparatus, and clinical research on applying the principle of the photoacoustic tomography apparatus to diagnose breast cancer or the like is energetically progressing.

In the case of photoacoustic tomography apparatus and ultrasonic diagnostic apparatus (apparatus for detecting acoustic waves reflected in living body and generating an image) which have been conventionally used in medical fields, images are usually generated using an average acoustic velocity of the subject (sound speed of acoustic wave inside the subject, propagation velocity of acoustic wave inside the subject or propagation speed of acoustic wave inside the subject). Generally sound speed is determined based on an experiential value or document-based values. However propagation speeds have individual differences, and sound speed also changes depending on the method of holding a subject, for example. Therefore if the sound speed used for generating an image and the actual sound speed are different, the resolution of an image drops considerably.

Patent Literature (PTL) 1, for example, discloses a way to solve this problem. According to the technology disclosed in Patent Literature (PTL) 1, sound speed is determined so that brightness or the contrast of each pixel (or voxel) is maximized. Thereby a drop in image quality, due to a mismatch of the sound speed used for generating the image and the actual sound speed, is suppressed.

However in the case of the technology in Patent Literature (PTL) 1, the brightness or contrast of the background noise also increases since the brightness or contrast of each pixel is maximized. Furthermore if noise is included in the detection signals, the sound speed is determined so that the total value of the noise component and normal signal component is maximized, therefore an accurate sound speed cannot be obtained, and the image blurs.

(PTL 1) Japanese Patent Application Laid-Open No. 2000-166925

SUMMARY OF INVENTION

The present invention provides an image generating apparatus and an image generating method which can generate an image representing information inside a subject, with suppressing a drop in image quality due to noise and a mismatch of the sound speed used for generating the image and the actual propagation velocity (sound speed).

The present invention in its first aspect provides an image generating apparatus comprising:

a probe having a plurality of detection elements which detect an acoustic wave propagating from inside a subject and output detection signals;

a determination unit that determines a propagation velocity of the acoustic wave inside the subject;

an image generating unit that generates an image representing information inside the subject using the propagation velocity determined by the determination unit and a plurality of detection signals obtained from the plurality of detection elements, wherein the determination unit sets a target area in a part of an area inside the subject, executes processing to adjust a phase of each of the detection signals based on a distance from each of the detection elements to the target area and a tentative velocity, and calculate dispersion of intensities of the plurality of detection signals of which phases are adjusted, for a plurality of tentative velocities, and determines a velocity for which dispersion of intensities is minimized, out of the plurality of tentative velocities, as the propagation velocity.

The present invention in its second aspect provides an image generating method comprising:

a step of detecting an acoustic wave propagating from inside a subject using a plurality of detection elements and generating detection signals;

a determination step of determining a propagation velocity of the acoustic wave inside the subject; and an image generating step of generating an image representing information inside the subject using the propagation velocity determined in the determination step and a plurality of detection signals obtained from the plurality of detection elements, wherein in the determination step, a target area is set in a part of an area inside the subject, processing to adjust a phase of each of the detection signals based on a distance from each of the detection elements to the target area and a tentative velocity, and calculate dispersion of intensities of the plurality of detection signals of which phases are adjusted, is executed for a plurality of tentative velocities, and a velocity for which dispersion of intensities is minimized, out of the plurality of tentative velocities, is determined as the propagation velocity.

The present invention in its third aspect provides a non-transitory computer readable medium recording a computer program for causing a computer to perform a method comprising:

a determination step of determining a propagation velocity of an acoustic wave inside a subject; and an image generating step of generating an image representing information inside the subject using a plurality of detection signals, which are generated by detecting an acoustic wave propagating from inside the subject using a plurality of detection elements, and the propagation velocity determined in the determination step, wherein in the determination step, a target area is set in a part of an area inside the subject, processing to adjust a phase of each of the detection signals based on a distance from each of the detection elements to the target area and a tentative velocity, and calculate dispersion of intensities of the plurality of detection signals of which phases are adjusted, is executed for a plurality of tentative velocities, and a velocity for which dispersion of intensities is minimized, out of the plurality of tentative velocities, is determined as the propagation velocity.

According to the present invention, an image representing information inside a subject can be generated with suppressing a drop in image quality due to noise and a mismatch of the velocity (sound speed) used for generating the image and the actual propagation velocity (sound speed).

Further features of the present invention will become apparent from the following description of exemplary embodiments with reference to the attached drawings.

BRIEF DESCRIPTION OF DRAWINGS

[FIG. 1]
[FIG. 2]
[FIG. 3]
[FIG. 4A]
[FIG. 4B]
[FIG. 5A]
[FIG. 5B]
[FIG. 6]
[FIG. 7A]
[FIG. 7B]

DESCRIPTION OF EMBODIMENTS

<Principle>

The principle of the present invention will now be described.

Figure 1:
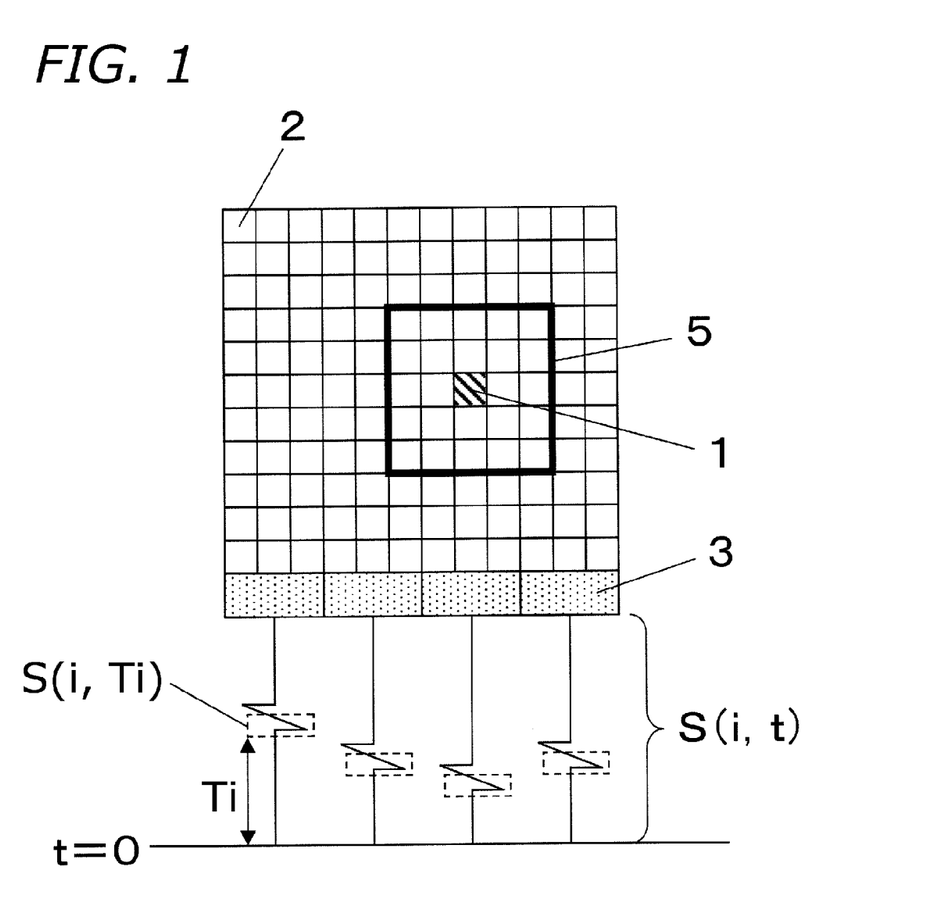
FIG. 1 is a diagram depicting a principle of the present invention.

FIG. 1 is a diagram depicting the principle of the present invention. In FIG. 1, the reference number 1 indicates a sound source (inside a subject), the reference number 2 indicates a voxel (or a pixel), and the reference number 3 indicates a detection element. Each detection element detects an acoustic wave propagating from the inside of the subject by a time sharing measurement, and outputs a detection signal. A number of the detection elements 3 is N (N is a 2 or higher integer).

Generally, an image generating apparatus using acoustic waves (ultrasonic waves) generates an image representing information inside a subject using a plurality of detection signals $S(i, t)$ obtained from a plurality of detection elements i. This kind of image is called a "generated image", and is also called "volume data" if the generated image is a three-dimensional image (an aggregate of voxels). A generated image is also called "pixel data" if it is a two-dimensional image. Each pixel (or voxel) of a generated image is normally calculated using a detection signal of which phase is adjusted based on a distance from each detection element to a position corresponding to the pixel and propagation velocity (sound speed) (or propagation velocity (sound speed) of the acoustic wave inside the subject). In the case of a Fourier domain method, however, an image is generated by operation in a frequency space. In FIG. 1, i denotes a number (integer in a 0 to N−1 range) of the detection element, and t denotes time.

Hereafter the time domain method, which is a general image generation method, will be described in concrete terms. First for each detection element, a distance from the i-th detection element to a position corresponding to a pixel in a generated image is divided by a sound speed. Using this result, time Ti for an acoustic wave reaches the detection element i (delay time) when the acoustic wave generated in this pixel position is calculated (generation time is assumed to be t=0). The intensity $S(i, Ti)$ of the detection signal at time Ti is calculated for each detection element, and the results are added, whereby the pixels of the generated image are generated (the generated image is generated by generating pixels for a plurality of positions in the same manner). According to the technology disclosed in Patent Literature (PTL) 1, the sound speed, that is the time Ti, is determined in this generated image generation method so that the data of each voxel (or pixel) is maximized. The intensity $S(i, Ti)$ indicates the intensity of the detection signal $S(i, t)$ at time Ti (intensity of the detection signal of which phase is adjusted).

Here if the sound speed estimated as the sound speed and the actual sound speed are significantly different, the intensity $S(i, Ti)$ disperses greatly. To prevent this, according to the present invention, a target area 5 (area to be targeted) is set in apart of an area inside the subject. Then processing of adjusting the phase of each detection signal $S(i, t)$, based on the distance from each detection element i to the target area 5 and a tentative sound speed, and calculating the dispersion of the intensities $S(i, Ti)$ of a plurality of detection signals of which phases are adjusted, is executed for a plurality of tentative sound speeds. Then a sound speed, out of the plurality of tentative sound speeds, of which the above mentioned dispersion of the intensity $S(i, Ti)$ is minimized, is determined as the sound speed, and the generated image is generated based on this sound speed.

For example, a coherent factor (CF) given by the following Expression (101) can be used as an index of the dispersion of the delay signal value.

[Math. 1]

$$CF = \frac{\left| \sum_{i=0}^{N-1} S(i) \right|^2}{N \sum_{i=0}^{N-1} |S(i)|^2} \quad (101)$$

Here $S(i)$ is an intensity of a detection signal which is output from the detection element i and of which phase is adjusted, that is an intensity $S(i, Ti)$ of the detection signal at time Ti which is calculated based on a sound speed. If $S(i)$ becomes a same value regardless the detection element, the index becomes CF=1, and as the dispersion of the value $S(i)$ increases, the index CF approaches closer to 0. In other words, as the dispersion of the intensity S (i, Ti) is greater, the value of the index CF becomes closer to 0, and as the dispersion is smaller, the value becomes closer to 1. In the present invention, a sound speed at which the dispersion of the intensity S (i, Ti) is minimized, that is a sound speed at which the index CF is the maximized is determined to be the sound speed. The index is not limited to CF. The dispersion may be evaluated with a scale which is used in statistical fields, such as a dispersion value and a standard deviation value.

Thus according to the present invention, the sound speed at which the dispersion of the intensity S (i, Ti) is minimized is set to the sound speed, whereby the generated image can be generated based on a sound speed closet to the actual sound speed. Also in the present embodiment, an increase in the background noise can be suppressed by limiting the area where the dispersion of the intensity S (i, Ti) is minimum. Further according to the present invention, the sound speed at which the dispersion of the intensity S (i, Ti) is minimized is regarded as the sound speed, so even if noise is randomly included in the detection signal, the noise can be equalized (in other words, the influence of noise can be minimized). As a result, even if noise is included in the detection signal, the actual sound speed can be accurately estimated.

Therefore according to the present invention, an image representing information inside a subject can be generated with suppressing a drop in image quality due to noise and a mismatch of the sound speed used for generating the image and the actual sound speed.

<Embodiments>

Figure 2:
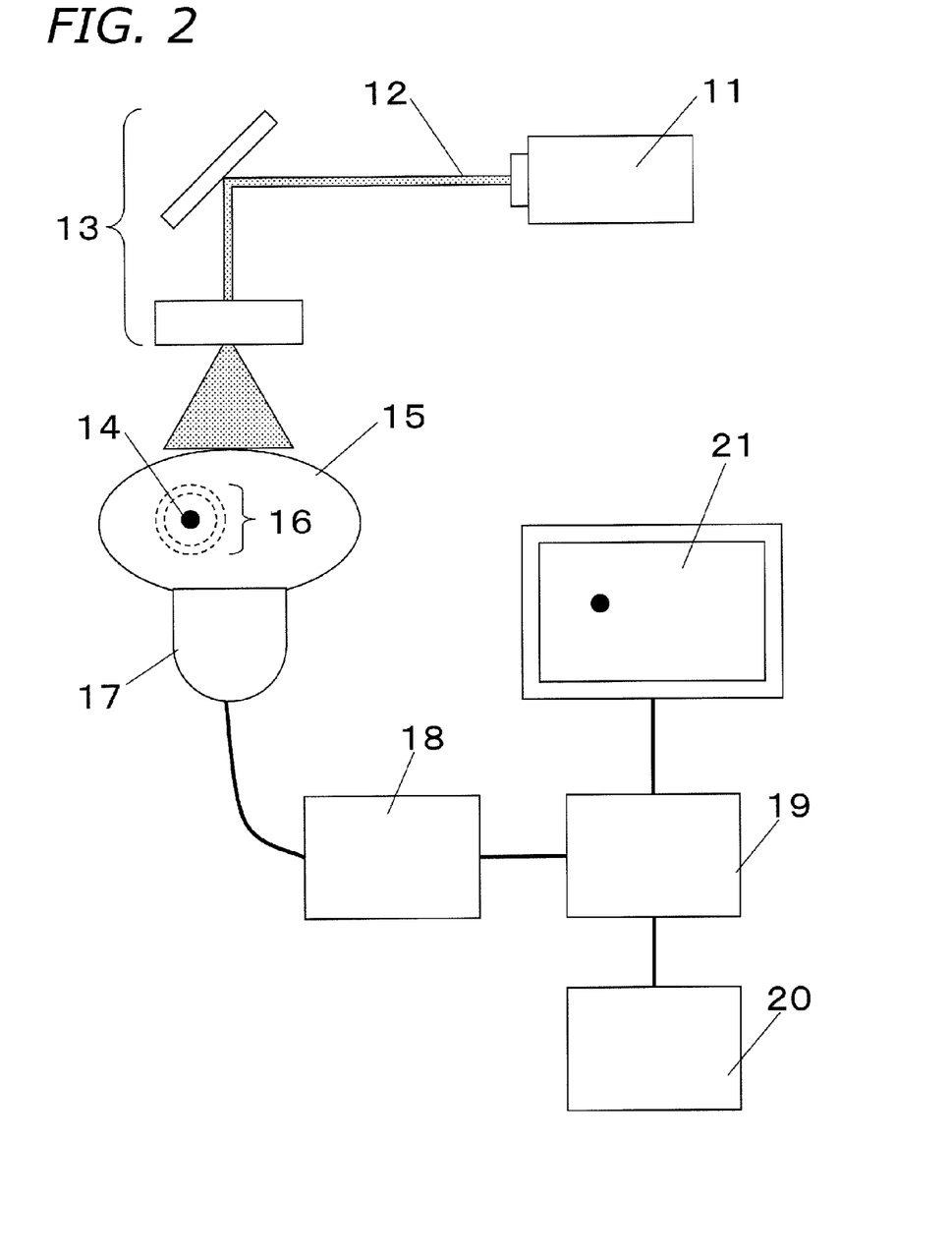
FIG. 2 is a diagram depicting an example of a configuration of an image generating apparatus according to the present embodiment.

Now an image generating apparatus and an image generating method according to the present embodiment will be described. FIG. 2 shows an example of a configuration of an image generating apparatus according to the present embodiment. Here a case of an image generating apparatus (photoacoustic tomography apparatus) using photoacoustic tomography technology, which detects an acoustic wave propagating from the inside of a subject and visualizes biological information, will be described as an example. The present invention can also be applied to an image generating apparatus using ultrasonic diagnostic technology (ultrasonic diagnostic apparatus), which generates an image of information representing the inside of a subject by transmitting an acoustic wave (ultrasonic wave) from an acoustic wave probe and detecting a reflected acoustic wave (ultrasonic wave) which is reflected inside the subject.

The image generating apparatus according to the present embodiment is comprised of a light source 11, an optical apparatus 13, an acoustic wave probe 17, a signal collector 18, an image generation processing unit 19, a signal processor 20 and a display apparatus 21. The light 12 emitted from the light source 11 (intensity modulated light) is irradiated onto a subject 15, such as a living body via the optical apparatus 13. When a part of the energy of the light propagating inside the subject 15 is absorbed by alight absorber (sound source) 14, such as a blood vessel, the acoustic wave (typically an ultrasonic wave) 16 is generated by thermal expansion of the light absorber 14. The generated acoustic wave 16 is detected by the acoustic wave probe 17, and the image of the biological information of the subject is generated by subsequent processing.

The light source 11 emits light having a specific wavelength which is absorbed by a specific component out of the components constituting the living body. The light source 11 may be integrated with the image generating apparatus according to the present embodiment, or may be a separate unit. The light source 11 is constituted by one or more pulsed light sources which can generated pulsed light in a several nano to several hundred nano second order. For the light source, a laser is preferable since a laser exhibits high output, but a light emitting diode or the like may be used instead of a laser. For the laser, various lasers can be used, including a solid-state laser, gas laser, dye laser and semiconductor laser. Irradiation timing, wave form of light, intensity and other factors are controlled by a control unit, which is not illustrated.

The light 12 emitted from the light source 11 is guided to the subject via the optical apparatus 13 (it may also be guided by an optical waveguide or the like). The optical apparatus 13 is, for example, a mirror which reflects light, and a lens which collects or spreads light. For this optical apparatus, any apparatus can be used only if the light 12 emitted from the light source can be irradiated to be a desired shape on the subject 15. Generally it is preferable to spread the light 12 to be a certain area, rather than collecting the light 12 by a lens, in terms of safety of a living body and having a wide diagnosis area. It is preferable that the area on which the light is irradiated on the subject (irradiation area) is movable (changeable). In other words, it is preferable that the image generating apparatus of the present embodiment is constructed such that the light generated from the light source can move on the subject. Then the generated image can be generated over a wider range. It is preferable that the irradiated area (light irradiated on the subject) can move synchronizing with the acoustic wave probe 17. Methods for moving the irradiation area are: using a movable mirror, and mechanically moving the light source itself among others are available.

The image generating apparatus according to the present embodiment is used for diagnosis of malignant tumors and vascular diseases of humans and animals, for example. Therefore as the subject 15, a diagnosis target area, such as a breast, finger and limb of humans and animals can be assumed. In the photoacoustic tomography apparatus, the light absorber (or sound source) 14 is a portion of the subject where an absorption coefficient is high. For example, in the case when the human body is a measurement target, oxygenated hemoglobin, reduced hemoglobin, blood vessels containing a high amount of these hemoglobins, and a malignant tumor which includes many new blood vessels, for example, could be the light absorbers. In the case of an ultrasonic diagnostic apparatus, the sound source 14 is a tissue interface of which acoustic impedance is different from the surrounding area.

The acoustic wave probe 17 has a plurality of detection elements. The detection element is constituted by a transducer utilizing piezoelectric phenomena, a transducer utilizing the resonance of light, or a transducer utilizing the change of capacity. Configuration is not limited to this, but can be any configuration that allows acoustic waves to be detected. In the acoustic wave probe 17, a plurality of detection elements are disposed typically in a one-dimensional or two-dimensional arrangement. By using the plurality of detection elements disposed like this, an acoustic wave can be detected in a plurality of locations all at once. Therefore the detection time can be decreased and such an influence as vibration of the subject can be minimized. If the acoustic wave is detected in a plurality of locations by moving the position of one detection element, signals (detection signals) similar to those in the case of using a plurality of detection elements can be obtained.

The signal collector 18 amplifies an electric signal (analog signal) obtained by the acoustic wave probe 17 (each detection element), and converts it into a digital signal (detection signal). The signal collector 18 is constituted typically by an amplifier, A/D converter and FPGA (Field Programmable Gate Array) chip among other components. It is preferable that a plurality of detection signals can be processed simultaneously. Then the time up to generating an image can be decreased.

The image generation processing unit 19 generates an image representing information inside the subject (generated image) using a plurality of detection signals (a plurality of digital signals which are output from the signal collector 18) obtained from a plurality of detection elements (the image generating unit). In each case of a general time domain method, each pixel of the generated image is calculated using: a detection signal of which phase is adjusted based on the distance from each detection element to a position corresponding to this pixel; and a sound speed which is determined by the later mentioned signal processor 20.

The signal processor 20 connected to the image generation processing unit 19 determines the sound speed of the acoustic wave inside the subject (the determination unit). According to the present embodiment, the sound speed is determined using a plurality of digital signals which are output from the signal collector 18 and the image obtained by the image generation processing unit 19.

The display apparatus 21 is an apparatus for displaying a generated image generated by the image generation processing unit 19. For the display apparatus 21, a liquid crystal display, a plasma display, an organic EL display and a display having electron-emitting devices, for example, can be used.

Figure 3:
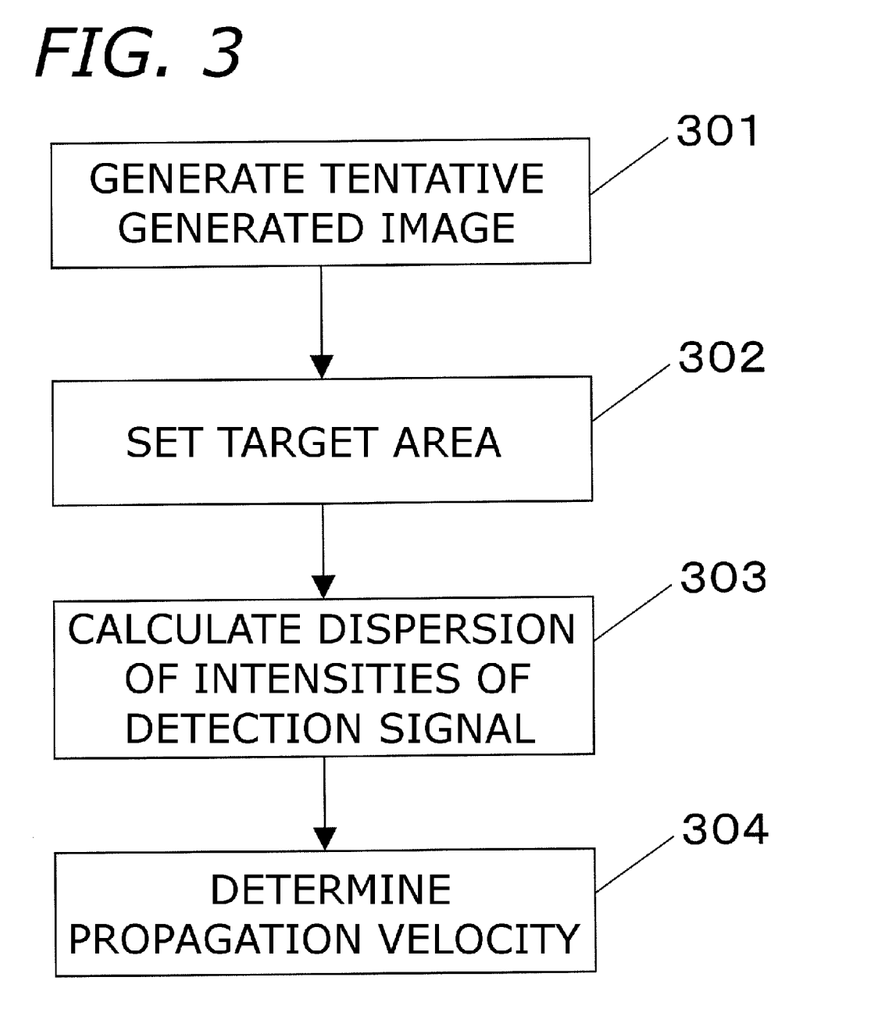
FIG. 3 is a flow chart depicting a method for generating a generated image.

Now processing by the image generation processing unit and the signal processor 20 will be described with reference to the flow chart in FIG. 3.

First the image generation processing unit 19 generates a tentative generated image (volume data) based on the estimated sound speed (predetermined sound speed) of the subject (step 301). For a method to generate a tentative generated image, methods conventionally used for a photoacoustic tomography apparatus and an ultrasonic diagnostic apparatus can be used. For example, a back projection method in a time domain or a Fourier domain can be used.

In step 301, it is preferable to use an image generating apparatus which generates a generated image by detecting an acoustic wave, such as an ultrasonic diagnostic apparatus and a photoacoustic tomography apparatus. However the present invention is not limited to this, and volume data (a generated image) on biological information may be generated using an image generating apparatus based on a different principle, such as an X-ray CT and MRI.

Then the signal processor 20 selects a pixel (target pixel) that strongly reflects the biological information out of the volume data (generated image) obtained in step 301, and determines an area which includes the position corresponding to the target pixel as the target area (step 302). In the case of a photoacoustic tomography apparatus, the target pixel is a pixel constituting the absorber, and in the case of an ultrasonic generated image, the target pixel is a pixel in an area where reflection of the ultrasonic wave is high.

The target pixel may be manually selected by the user checking the generated image, or may be automatically selected. In the case of automatically selecting the target pixel, a pixel of which luminance or contrast is highest in the image, for example, is selected as the target pixel.

The size of the target area is determined based on the later mentioned selection range of the tentative sound speed. For example, a case of obtaining a generated image using a 1500 m/sec. sound speed (estimated sound speed $c_0$: predetermined sound speed), then switching the sound speed to another sound speed (tentative sound speed) in the 1400 to 1600 m/sec. range and regenerating the image, is considered. Here the pixel pitch d is 0.25mm, and thickness r of the subject (distance from the position in the subject corresponding to the target pixel to the acoustic wave probe) is 40 mm. In this case, it is possible that the position corresponding to the target pixel shifts about 10 pixels at the maximum in the x, y and z directions. In such a case, an area corresponding to the range including 10 pixels from the target pixel in the x, y and z directions (e.g. range including 21*21*21 pixels around the target pixel) is selected as the target area.

In concrete terms, a position corresponding to the target pixel in the case of using estimated sound speed $c_0$ (predetermined sound speed) changes for about M pixel in width from this position if the sound speed to be used is changed. The value M is obtained by the following Expression (102). In Expression (102), $c_{min}$ is a minimum value of the tentative sound speed, and $c_{max}$ is a maximum value of the tentative sound speed.

[Math. 2]

$$M = \frac{c_0}{d}\left(\frac{r}{c_{min}} - \frac{r}{c_{max}}\right) \quad (102)$$

Therefore the area corresponding to the range of width M obtained by Expression (102) around the target pixel can be set as the target area. In other words, if a three-dimensional image is generated, an area corresponding to the range which includes M*M*M voxels around the target pixel is selected as the target area. If a two-dimensional image is generated, an area corresponding to the range which includes M*M pixels around the target pixel is selected as the target area. Thereby an area which includes a sound source, such as an absorber, can be the target area.

The thickness r of the subject in Expression (102) is specifically a distance from a position corresponding to the target pixel to a detection element which is most distant from this position. The thickness of the subject however is not limited to this, but may be a distance from the position corresponding to the target pixel to a detection element which is closest to this position. Or the thickness of the subject may be an average of the distance between the position corresponding to the target pixel and each detection element.

Then the signal processor 20 adjusts the phase of each detection signal based on the distance from each detection element to the target area (e.g. a position in the target area corresponding to a pixel of the generated image) and a tentative sound speed. Then the signal processor 20 calculates the dispersion of the intensities of a plurality of detection signals of which phases are adjusted (step 303). The processing in step 303 is executed for a plurality of tentative sound speeds.

Then the signal processor 20 determines a sound speed of which dispersion of intensity is minimized, out of the plurality of tentative sound speeds, as the sound speed (step 304). The image generation processing unit 19 generates the generated image based on the determined sound speed.

By the above processing, image representing information inside the subject can be generated with suppressing a drop in image quality due to noise and mismatch of the sound speed used for generating the image and actual sound speed.

Figure 4A:
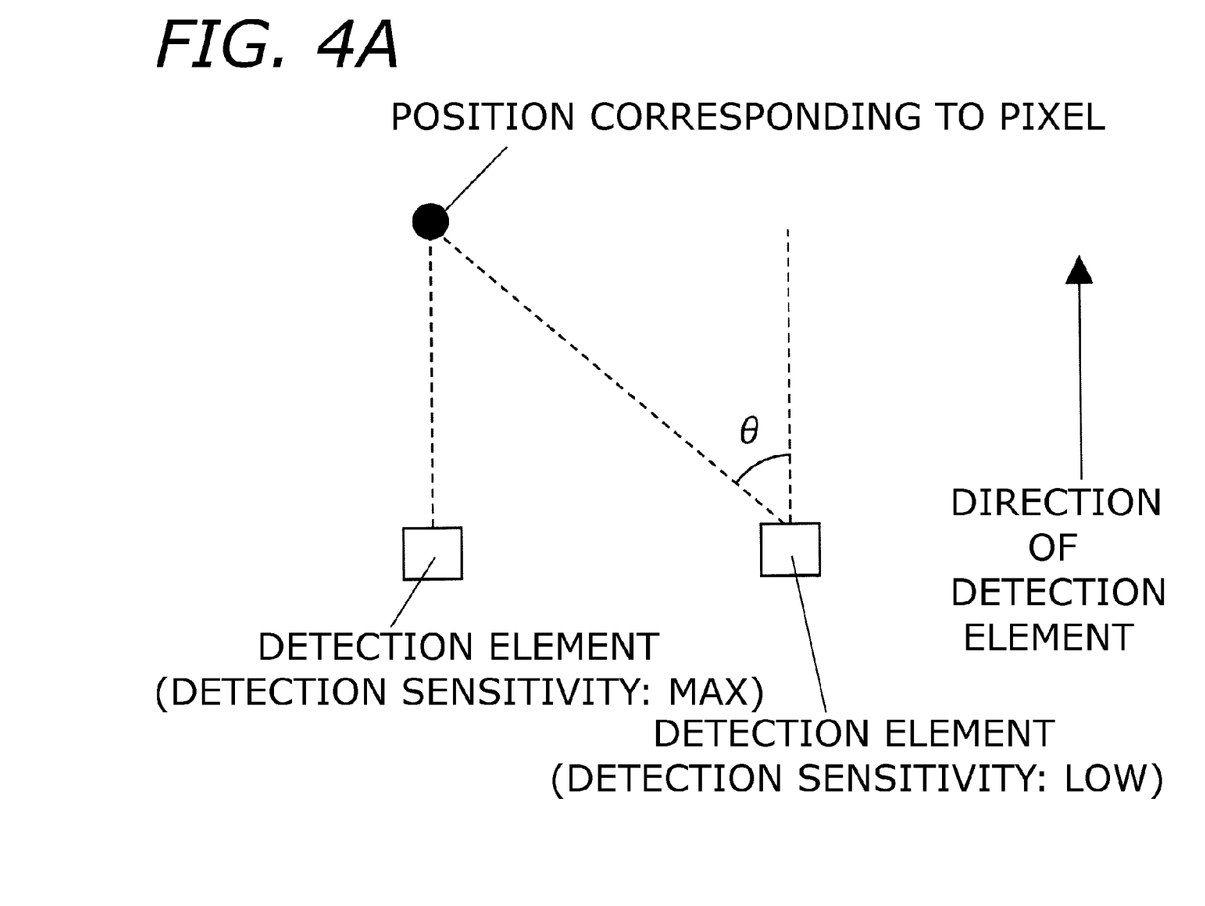
FIG. 4A is a diagram depicting an example of the positional relationship of a detection element and a processing target position.

If the area of the detection element is large, the detection signal is strongly influenced by the directivity. Directivity will be described with reference to FIG. 4A and FIG. 4B. Directivity is a characteristic where the detection sensitivity of the detection element changes depending on the relative positional relationship between the detection element and a position inside the subject (position corresponding to the pixel: processing target position). For example, if the detection element is facing the processing target position as shown in FIG. 4A, the sensitivity to detect the acoustic wave from this position is at the maximum (intensity of the detection signal is at the maximum). As the deviation between the direction of the detection element and the processing target position becomes greater, the detection sensitivity decreases (intensity of the detection signal decreases). This influence of directivity becomes conspicuous when the width of the element is large, or when the frequency of the acoustic wave to be detected is high. Directivity R (detection sensitivity) is given by the Expression (103).

[Math. 3]

$$R = \left| \frac{\sin(k \cdot d \sin\theta)}{k \cdot d \sin\theta} \right| \quad (103)$$

d: width of detection element
θ: angle formed by the line connecting the processing target position and the detection element and the direction of the detection element
k: $2\pi/\lambda$
λ: wavelength of acoustic wave The shape of the detection element is assumed to be a square.

Figure 4B:
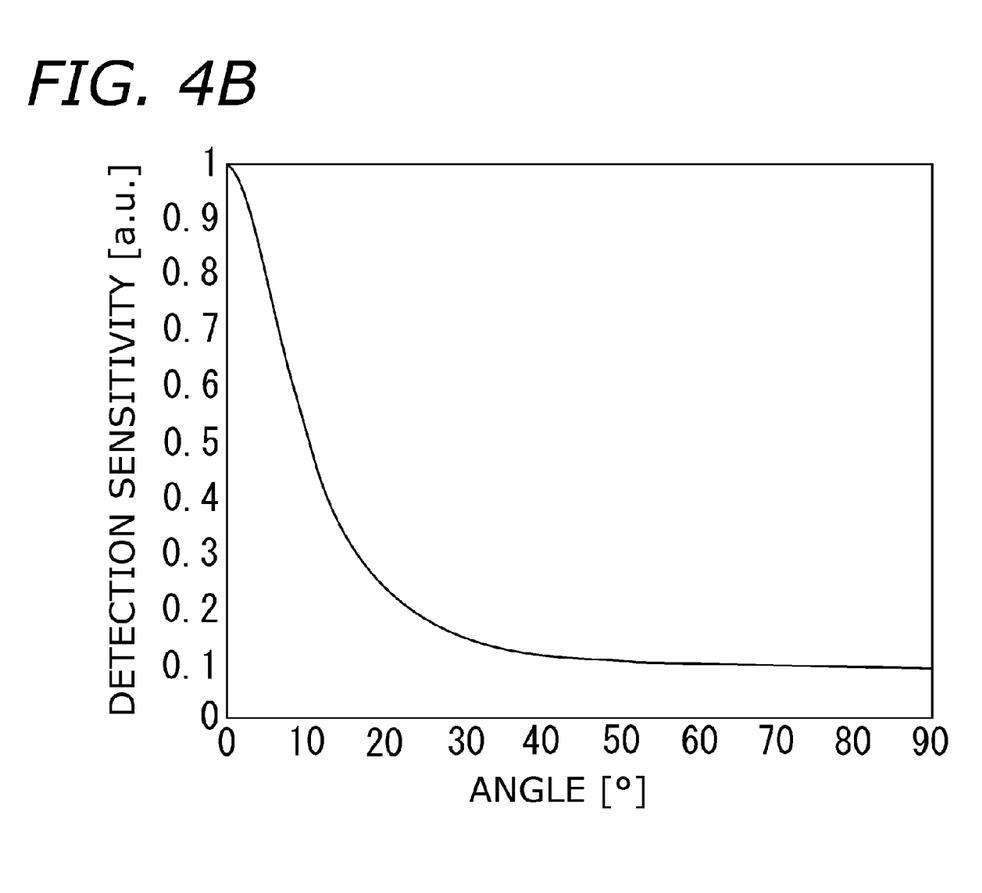
FIG. 4B is a graph depicting an example of the directivity of the detection element.

FIG. 4B shows an example of the directivity of the detection element of which the element width is 2 mm. Here a magnitude of each frequency component is calculated using the frequency characteristic obtained from the impulse response of the detection element, and a directivity (detection sensitivity standardized with maximum value 1) is calculated using Expression (103). As FIG. 4B shows, the sensitivity (intensity of detection signal) suddenly drops if the angle formed by the line connecting the processing target position and detection element and the direction of the detection element increases. Such directivity increases dispersion among detection signals.

Therefore it is preferable that the image generating apparatus of the present embodiment further has a function to correct the drop in intensity of the detection signal due to the directivity of the detection element, according to the relative positional relationship of the position corresponding to the pixel and detection element. And it is preferable that the signal processor 20 determines the sound speed using the detection signal of which intensity is corrected, and the image generation processing unit 19 generates the image using the detection signal, of which intensity is corrected. Thereby the influence of directivity of the detection element can be suppressed. For example, dispersion of the detection signals due to directivity can be decreased (dispersion due to sound speed becomes dominant), so the sound speed can be determined more accurately. Also the dispersion of intensity of the detection signal due to directivity is decreased, so an image of which image quality does not drop can be generated.

For correction, the angle formed by the line connecting the processing target position and the detection element and the direction of the detection element is calculated based on the relative positional relationship of the processing target position and the detection element, for example, and intensity of the detection signal, which is output from the detection element, is increased based on the value of the directivity according to the angle (e.g. value of the Y axis in FIG. 4B). In concrete terms, the detection signal is multiplied by the inverse number of the value of directivity. Then dispersion of intensity of the detection signal due to directivity can be suppressed.

In many cases, the processing of the image generation processing unit 19 and the signal processor 20 are implemented by the processing unit of a computer (e.g. workstation) executing software (programs). Therefore the image generation processing unit 19 and the signal processor 20 may not be distinguished. These functional elements may be constructed by a dedicated chip respectively.

The processing of the image generation processing unit 19 and the signal processor 20 maybe implemented by hardware instead of software.

According to the present embodiment, the target area is determined using the position of the target pixel and Expression (102), but the present invention is not limited to this. If a general location of the target area can be estimated, such as the case when a predetermined subject is measured, information on the target area may be stored in the apparatus in advance. Information on the predetermined target area maybe stored in advance for each type (measuring area) of subject. In such a case, the tentative generated image in step 301 of the present embodiment need not be generated. The target area can be any size (even a one pixel size). For example, the target area can be set so that the position corresponding to the target pixel selected in step 302 is included. Since the sound source is assumed to have a certain size, the target area set like this can receive sound from the sound source even if the position corresponding to the target pixel is shifted to outside the target area by a change in sound speed.

EXAMPLE 1

The present invention is simulated, and the effect thereof is verified. This example will be described with reference to FIG. 5A, FIG. 5B and FIG. 6.

Figure 5A:
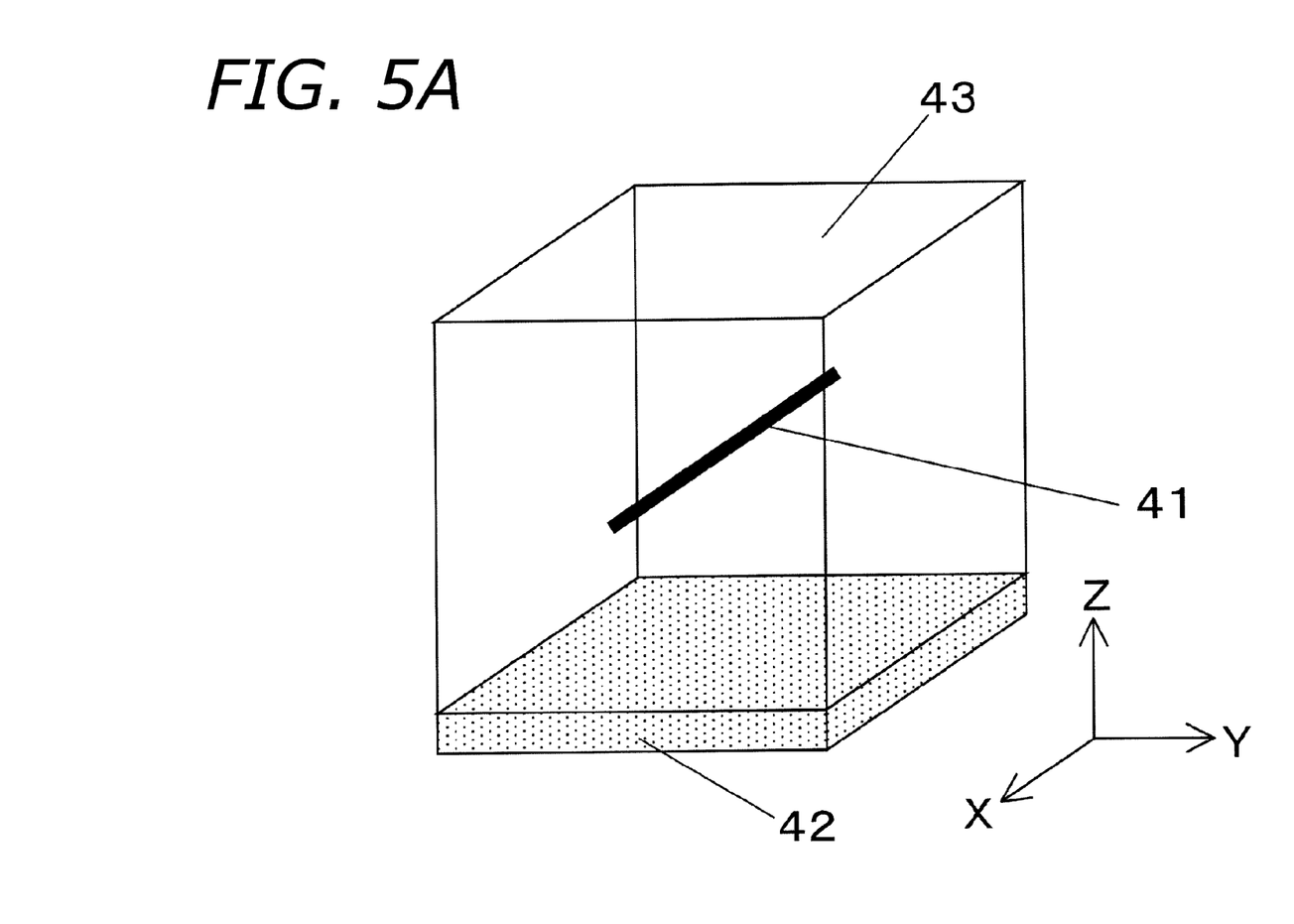
FIG. 5A is a diagram depicting an example of simulation conditions according to Example 1.

As a subject, a cubic phantom 43 of which X direction: 4 cm, Y direction: 4 cm and Z direction: 4 cm, is used, as shown in FIG. 5A. At the center of the cubic phantom 43, a cylindrical sound source 41, of which diameter is 0.05 cm and height is 2 cm, is disposed so that the axis direction thereof is parallel with the X direction. Here the sound source 41 is a light absorber in the case of photoacoustic tomography, and an ultrasonic reflector in the case of an ultrasonic diagnostic apparatus. It is assumed that the sound speed of the acoustic wave inside the subject is 1500 m/sec., and the initially generated sound pressure, which is generated in the sound source 41, is 3000 Pa (pascal).

The acoustic wave probe 42 is a two-dimensional array type and is constituted by 20*20 square detection elements. The length of one side of each element is 2 mm, and the pitch distance is 2 mm. It is assumed that the acoustic wave is detected with a sampling frequency of 20 MHz at 1280 measurement points.

Figure 5B:
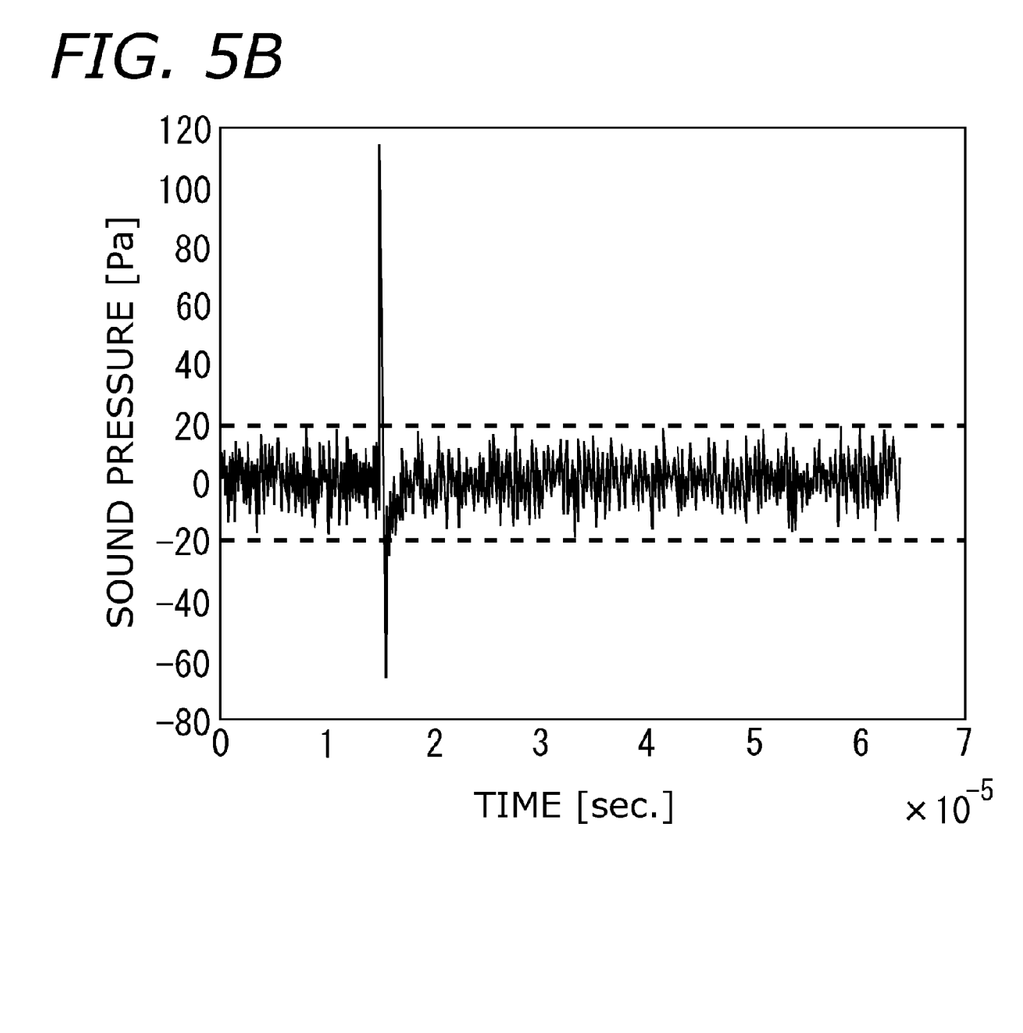
FIG. 5B is a graph depicting an example of a detection signal of the simulation according to Example 1.

Under the above conditions, the detection signal of the acoustic wave detected by each element of the acoustic wave probe 42 is generated by physical simulation. FIG. 5B shows an example of the detection signal obtained by the detection element at the center of the probe. The strong signal in FIG. 5B indicates a signal from the sound source 41. It is assumed that the detection signal includes a white noise, in which the tripled standard deviation is 20 Pa.

Using a detection signal obtained in this way and a sound speed (predetermined sound speed) of 1580 m/sec., a generated image is generated. For the generation method, a universal back projection according to a time domain method, which is a publicly known technology, is used. The imaging range is X direction: 3.8 cm, Y direction: 3.8 cm and Z direction: 4 cm, and the pixel pitch (voxel pitch) is 0.025 cm. A total number of voxels is aquired by dividing the imaging range by the voxel pitch, that is 152*152*160.

Figure 6:
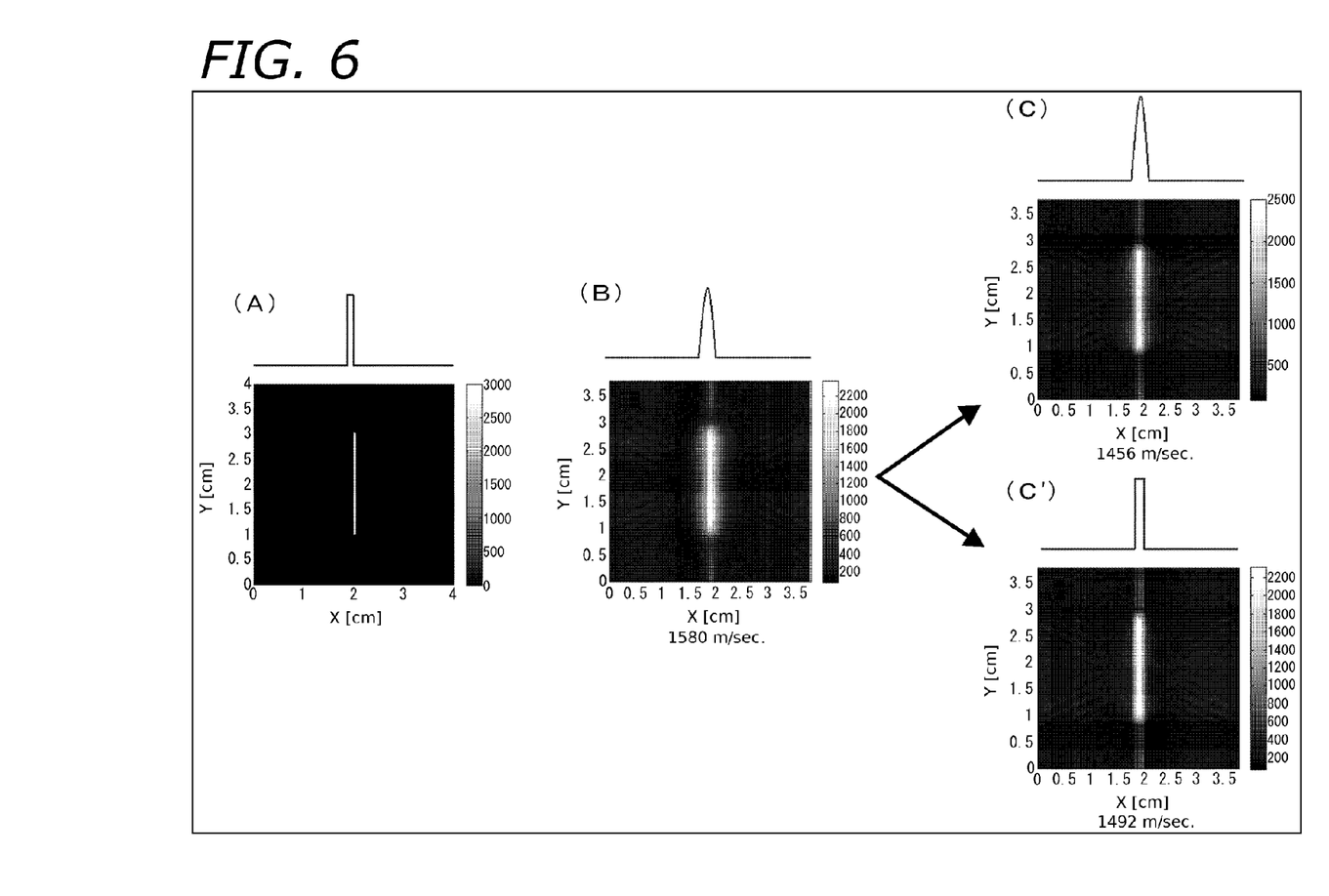
FIG. 6 shows an example of the images generated in simulation according to Example 1.

FIG. 6 shows the generated images. All the images shown in FIG. 6 are MIP (Maximum Intensity Projection) images in which maximum intensity of voxel values are projected in the direction of the acoustic wave probe 42, and the white area indicates high sound pressure. The change of sound pressure of the image in the X direction at Y=2.0 cm is shown above each image.

In FIG. 6, the image A shows an MIP image of the sound source inside the subject. According to this example, it is assumed that the resolution is higher as the image is closer to image A.

Image B is a generated image obtained when a 1580 m/sec. sound speed is used as the sound speed. As this image shows, if a sound speed different from the actual sound speed of 1500 m/sec. is used, the image blurs and resolution drops.

Then in this image (volume data), a voxel of which luminance is maximum is searched. As a result, the voxel at the center (76*76*80$^{th}$ voxel in all the voxels of 152*152*160) is detected. The area corresponding to 21*21*21 voxels centering around this voxel is set as the target area.

Then in order to compare with prior art, the luminance value is calculated for each position (voxel) in the target area, while changing the sound speed to be used from 1400 m/sec. to 1600 m/sec. at a 2 m/sec. interval. In other words, 21*21*21*101 number of luminance values are calculated. As a result, the sound speed at which the luminance value is maximized is 1456 m/sec. Then using this sound speed 1456 m/sec., an image is generated again. Image C is an image obtained at this time. The image is somewhat blurred, but resolution is slightly improved compared with image B. The maximum luminance value also increases.

In order to substantiate the effect of the present invention, the dispersion of intensity (index CF) of the detection signal is calculated for each position (voxel) in the target area while changing the sound speed to be used from 1400 m/sec. to 1600 m/sec. at a 2 m/sec. interval. In other words, 21*21*21*101 number of index CFs are calculated. As a result, the sound speed at which the index CF is maximized is 1492 m/sec. Then using this sound speed of 1492 m/sec., the image is generated again. Image C' is an image obtained at this time. Compared with image C, which is the prior art, image blur is less and resolution improves.

Table 1 shows this result.

TABLE 1

|  | Velocity | Image quality (amount of blur) |
| --- | --- | --- |
| Image A (actual image) | 1500 m/sec. | None |
| Image B (estimate) | 1580 m/sec. | High |
| Image C (prior art) | 1456 m/sec. | Mid- |
| Image C' (this example) | 1492 m/sec. | Low |

In this way, according to the present invention, a sound speed close to the actual sound speed (1492 m/sec.) can be estimated. Particularly in a detection signal containing noise, a sound speed closer to the actual sound speed can be estimated than the sound speed obtained by the prior art (1456 m/sec.). As a result, an image without a drop in resolution can be obtained.

The sound speed is estimated as 1492 m/sec. while the actual sound speed is 1500m/sec., because of the influence of noise and directivity of the detection element.

In this example, dispersion of the intensity of the detection signals is calculated for each position in the target area, but the dispersion maybe calculated for a part of the positions in the target area. For example, the dispersion may be calculated only for the center position of the target area.

EXAMPLE 2

An example of applying the present invention to a photoacoustic tomography apparatus will now be described with reference to FIG. 2. In this example, a Q switch YAG laser, which generates a pulsed light with a 1064 nm wavelength for about 10 nano seconds, is used as a light source 11. The energy of the pulsed laser beam (light 12) is 0.6 J, and this pulsed light spreads to about a 2 cm radius using an optical apparatus 13 such as a mirror and a beam expander. For a subject 15, a phantom simulating a living body is used. The phantom used is 1% intralipid solidified with agar. The size of the phantom is width: 12 cm, height: 8 cm and depth: 4 cm. In this phantom, a black rubber wire with a 0.03 cm diameter is embedded as a light absorber 14 in the center area. Light 12, which is spread to a 2 cm radius, is irradiated onto this phantom. For the acoustic wave probe 17, an ultrasonic transducer made from PZT (lead zirconate titanate) is used. This transducer is a two-dimensional array type, where a number of elements is 18*18, the shape of each element is square, and the element pitch is 2 mm. The width of each element is about 2 mm. This acoustic wave probe can move in the X and Y directions synchronizing with the light irradiation area, so as to image a large area.

Figure 7A:
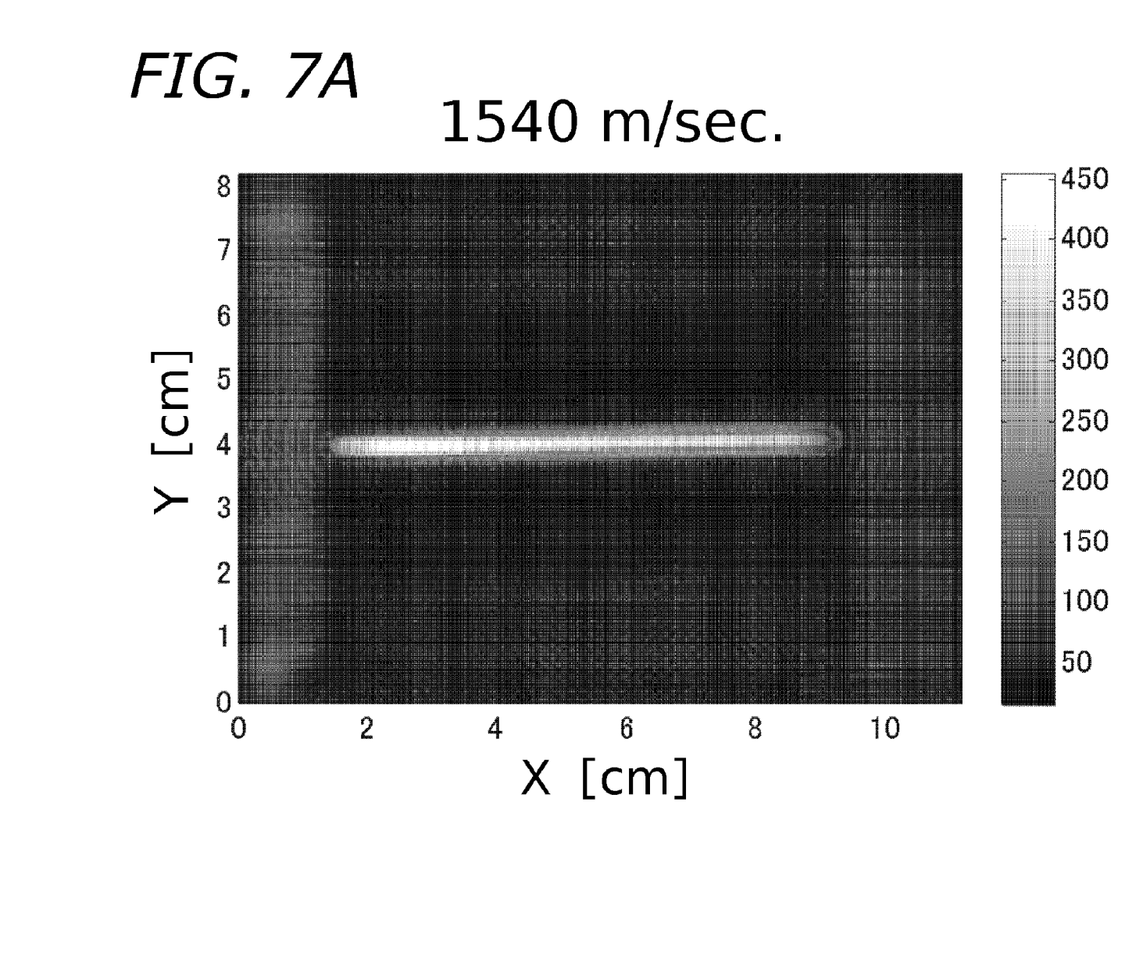
FIG. 7A shows an example of the image generated by an image generating apparatus according to Example 2.

If a pulsed light is irradiated onto one surface of the phantom, the light diffused inside the phantom is absorbed by the rubber wire, and a photoacoustic wave is generated. This photoacoustic wave is detected by each ultrasonic transducer having 324 channels, and the digital data (detection signal) of the photoacoustic wave is obtained for each channel, using a signal collector 18, which is comprised of an amplifier, A/D converter and FPGA. In order to improve the S/N ratio of the signal, the laser is irradiated 36 times, and all obtained detection signals are averaged. Then the obtained digital data is transferred to a workstation (WS), which is an image generation processor 19 and a signal processor 20, and the WS stores this data. After performing noise reduction processing on this stored data by discrete wavelet transformation, the image is generated using a 1540 m/sec. sound speed, which is an average sound speed of an acoustic wave inside living body. Here volume data is generated using a universal back projection method, which is a time domain method. The voxel pitch used in this case is 0.05 cm. The imaging range is set to 11.8 cm*11.8 cm*4.0 cm. FIG. 7A shows an example of the obtained image.

Figure 7B:
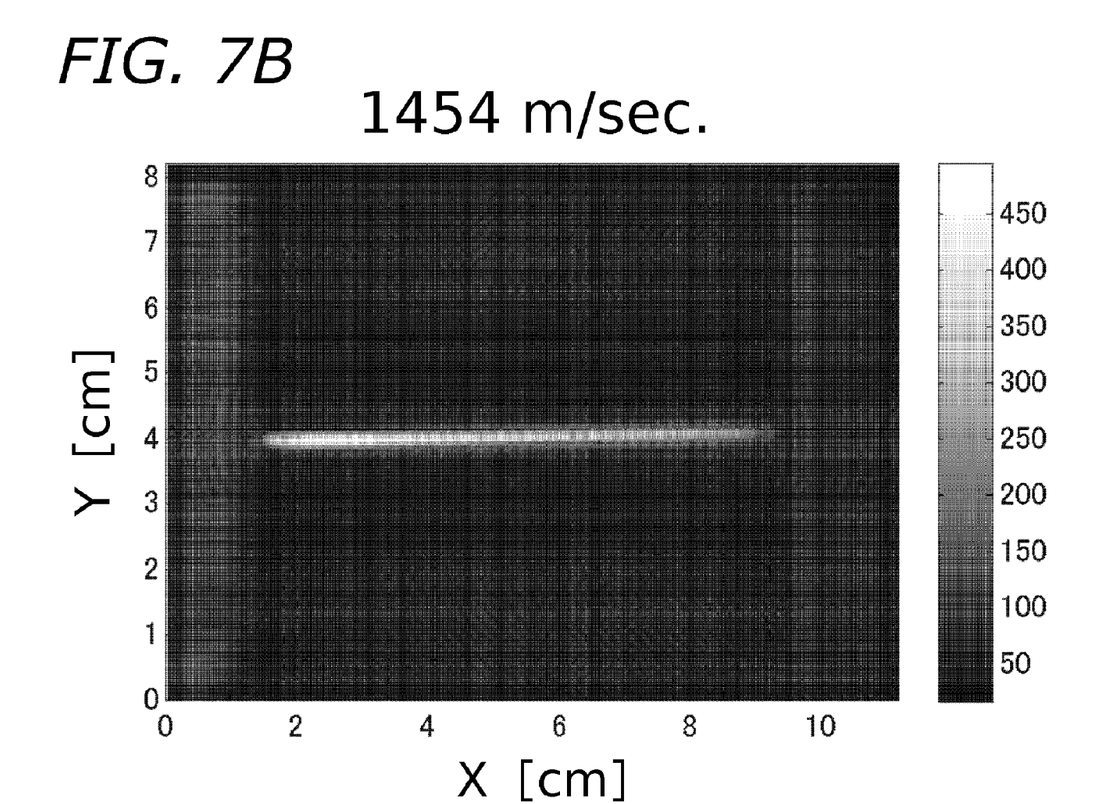
FIG. 7B shows an example of the image generated by the image generating apparatus according to Example 2.

Then the dispersion of intensity (index CF) of the detection signal is calculated for each position (voxel) in the target area, while changing the sound speed to be used from 1400 m/sec. to 1600 m/sec. at a 2 m/sec. interval. According to this example, in the obtained volume data, an area corresponding to the voxel group (21*21*21 voxels), which includes the sound wave (initial sound pressure) generated in the wire, is set as the target area. Also according to this example, the detection signal is corrected considering the directivity calculated based on the impulse response of the detection element, and the index CF is calculated using the corrected detection signal. The maximum index CF improved from 0.056 to 0.078 by considering the directivity. In this example, the sound speed at which the index CF becomes maximum is 1454 m/sec. Then using this 1454 m/sec. sound speed and the detection signal stored in a PC, an image is generated again. The obtained image is displayed on a liquid crystal display, which is a display apparatus 21.1 FIG. 7B shows an example of the obtained image.

As the above result shows, the width of the acoustic wave (initial sound pressure) generated from the rubber wire is obviously narrower in the image generated using a 1454 m/sec. sound speed (FIG. 7B) than in the image generated using a 1540 m/sec. sound speed (FIG. 7A). It is clear that there is hardly any image blur, in other words, resolution improved.

In this way, according to this example, the sound speed of the acoustic wave inside the subject can be accurately estimated, and therefore resolution of the generated image can be improved.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-281452, filed on Dec. 11, 2009, which is hereby incorporated by reference herein in its entirety.

The invention claimed is:

1. An image generating apparatus, comprising:
a probe having a plurality of detection elements which detect an acoustic wave propagating from inside a subject and output detection signals;
a determination unit that determines a propagation velocity of the acoustic wave inside the subject; and
an image generating unit that obtains an image representing information inside the subject using the propagation velocity determined by said determination unit and a plurality of detection signals obtained from said plurality of detection elements,
wherein said determination unit
sets a target area in a part of an area inside the subject,
sets a tentative propagation velocity,
adjusts a phase of each of the detection signals based on a distance from each of said detection elements to the target area and the tentative propagation velocity, and obtains dispersion of intensities of the plurality of detection signals whose phases are adjusted, and
determines the propagation velocity based on the dispersion of intensities.

2. The image generating apparatus according to claim 1, wherein said determination unit
executes processing to adjust a phase of each of the detection signals based on a distance from each of the detection elements to the target area and a tentative propagation velocity, and obtain dispersion of intensities of the plurality of detection signals of which phases are adjusted, for a plurality of tentative propagation velocities, and
determines a propagation velocity for which dispersion of intensities is minimized, out of the plurality of tentative propagation velocities, as the propagation velocity.

3. The image generating apparatus according to claim 2, wherein said determination unit
sets a target pixel having the highest luminance value or contrast, out of each pixel of the image representing information inside the subject, generated based on a predetermined propagation velocity,
sets an area which is around the target pixel and corresponds to a range of pixels having width M given by the following expression as the target area:

[Math. 2]

$$M = \frac{c_0}{d}\left(\frac{r}{c_{min}} - \frac{r}{c_{max}}\right)$$

where $c_{min}$ is a minimum value and $c_{max}$ is a maximum value out of the plurality of tentative propagation velocities, d is a pixel pitch, r is a distance from the probe to the position corresponding to the target pixel, and $c_0$ is the predetermined propagation velocity.

4. The image generating apparatus according to claim 1, wherein said determination unit sets an area which includes a position corresponding to a target pixel having the highest luminance value or contrast, out of each pixel of the image representing information inside the subject, generated based on a predetermined propagation velocity as the target area.

5. The image generating apparatus according to claim 1, further comprising
a correction unit that corrects a drop in the intensity of the detection signal due to directivity of one of said detection element according to a relative positional relationship between a position corresponding to a pixel and that detection element,
wherein said determination unit determines the propagation velocity using the detection signal whose intensity is corrected.

6. The image generating apparatus according to claim 1, wherein said determination unit determines a propagation velocity whose index CF represented by the following expression is maximized as the propagation velocity:

[Math. 1]

$$CF = \frac{\left|\sum_{i=0}^{N-1} S(i)\right|^2}{N\sum_{i=0}^{N-1} |S(i)|^2}$$

where N (N is an integer that is 2 or greater) is the number of said detection elements, and S(i) (i is an integer in a range from 0 to N−1) is an intensity of a detection signal which is output from the i-th one of said detection elements and whose phase is adjusted.

7. The image generating apparatus according to claim 1, wherein said image generating unit calculates each pixel of the image using a detection signal whose phase is adjusted based on a distance from each detection element to a position corresponding to the pixel and the determined propagation velocity.

8. The image generating apparatus according to claim 1, wherein the acoustic wave propagating from inside the subject is an acoustic wave generated by intensity modulated light from a light source with which the subject is irradiated.

9. An image generating method, comprising:
- a step of detecting an acoustic wave propagating from inside a subject using a plurality of detection elements and generating detection signals;
- a determination step of determining a propagation velocity of the acoustic wave inside the subject; and
- an image generating step of generating an image representing information inside the subject using the propagation velocity determined in said determination step and a plurality of detection signals obtained from the plurality of detection elements,
- wherein, in said determination step,
  - a target area is set in a part of an area inside the subject,
  - a tentative propagation velocity is set,
  - a phase of each of the detection signals is adjusted based on a distance from each of the detection elements to the target area and the tentative propagation velocity,
  - dispersion of intensities of the plurality of detection signals of which phases are adjusted is obtained, and
  - a propagation velocity is determined based on the dispersion of intensities.

10. The image generating method according claim 9, wherein, in said determination step,
- processing to adjust a phase of each of the detection signals based on a distance from each of the detection elements to the target area and the tentative propagation velocity, and obtain dispersion of intensities of the plurality of detection signals whose phases are adjusted, is executed for a plurality of tentative propagation velocities, and
- a propagation velocity for which dispersion of intensities is minimized, out of the plurality of tentative propagation velocities, is determined as the propagation velocity.

11. A non-transitory computer readable medium storing, in executable form, a computer program for causing a computer to perform the image generating method according to claim 9.

* * * * *